(12) United States Patent
Bui et al.

(10) Patent No.: US 9,789,055 B2
(45) Date of Patent: *Oct. 17, 2017

(54) SOLID LIPSTICK COMPOSITION HAVING IMPROVED HARDNESS

(71) Applicant: L'OREAL, Paris (FR)

(72) Inventors: Hy Si Bui, Piscataway, NJ (US); Rita Jaky El-Khouri, Morristown, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,815

(22) Filed: Jun. 18, 2014

(65) Prior Publication Data

US 2015/0366779 A1 Dec. 24, 2015

(51) Int. Cl.
| | |
|---|---|
| *A61K 8/89* | (2006.01) |
| *A61Q 1/06* | (2006.01) |
| *A61K 8/92* | (2006.01) |
| *A61K 8/31* | (2006.01) |
| *A61K 8/58* | (2006.01) |
| *A61K 8/891* | (2006.01) |
| *A61K 8/02* | (2006.01) |

(52) U.S. Cl.
CPC .............. *A61K 8/92* (2013.01); *A61K 8/0229* (2013.01); *A61K 8/31* (2013.01); *A61K 8/585* (2013.01); *A61K 8/891* (2013.01); *A61Q 1/06* (2013.01)

(58) Field of Classification Search
None
See application file for complete search history.

(56) References Cited

U.S. PATENT DOCUMENTS

| | | | |
|---|---|---|---|
| 4,693,935 A | 9/1987 | Mazurek | |
| 4,972,037 A | 11/1990 | Garbe et al. | |
| 4,981,902 A | 1/1991 | Mitra et al. | |
| 4,981,903 A | 1/1991 | Garbe et al. | |
| 5,061,481 A | 10/1991 | Suzuki et al. | |
| 5,209,924 A | 5/1993 | Garbe et al. | |
| 5,219,560 A | 6/1993 | Suzuki et al. | |
| 5,262,087 A | 11/1993 | Tachibana et al. | |
| 5,468,477 A | 11/1995 | Kumar et al. | |
| 5,849,275 A | 12/1998 | Calello et al. | |
| 5,919,879 A | 7/1999 | Midha et al. | |
| 6,033,650 A | 3/2000 | Calello et al. | |
| 6,555,117 B2 | 4/2003 | Midha et al. | |
| 7,879,316 B2 | 2/2011 | Ferrari et al. | |
| 8,586,013 B2 | 11/2013 | Bradshaw et al. | |
| 8,603,444 B2 | 12/2013 | Bui | |
| 2003/0235552 A1 | 12/2003 | Yu | |
| 2004/0151680 A1* | 8/2004 | Patil | A61K 8/891 424/70.12 |
| 2004/0156806 A1 | 8/2004 | Patil et al. | |
| 2005/0089498 A1 | 4/2005 | Patil et al. | |
| 2006/0292096 A1 | 12/2006 | Yu | |
| 2007/0093619 A1* | 4/2007 | Bui | A61K 8/891 525/477 |
| 2010/0310490 A1* | 12/2010 | Barba | A61K 8/891 424/70.121 |
| 2012/0171137 A1 | 7/2012 | Bradsaw et al. | |
| 2012/0288462 A1* | 11/2012 | Lebok | A61K 8/0229 424/64 |
| 2012/0301415 A1 | 11/2012 | Bui et al. | |
| 2013/0171084 A1 | 7/2013 | Kawaratani et al. | |

FOREIGN PATENT DOCUMENTS

| | | |
|---|---|---|
| WO | 93/23446 A2 | 11/1993 |
| WO | 95/06078 A1 | 3/1995 |
| WO | 01/32727 A1 | 5/2001 |
| WO | 01/32737 A1 | 5/2001 |

OTHER PUBLICATIONS

I. Van Reeth, K.F. Zhikai, T. Leaym, F. Lin, Dow Corning Corporation; New Silicone Resin Film Formers for Longer Wear and Enhanced Comfort; www.dowcorning.com/personalcare.
R. Canterbery Pepe, J.A. Wenninger, G.N. McEwen, Jr.; International Cosmetic Ingredient Dictionary and Handbook, Ninth Edition, 2002; The Cosmetic, Toiletry, and Fragrance Association, 1101 17th Street, NW, Suite 300, Washington, DC 20036-4702; www.ctfa.org.
International Search Report and Written Opinion dated Aug. 27, 2015 in PCT/EP2015/063678.
U.S. Appl. No. 14/307,815, filed Jun. 18, 2014, Hy Si Bui.
U.S. Appl. No. 14/307,831, filed Jun. 18, 2014, Hy Si Bui.
U.S. Appl. No. 14/307,851, filed Jun. 18, 2014, Hy Si Bui.

* cited by examiner

*Primary Examiner* — Robert A Wax
*Assistant Examiner* — Danah Al-Awadi
(74) *Attorney, Agent, or Firm* — Oblon, McClelland, Maier & Neustadt, L.L.P.

(57) ABSTRACT

Disclosed is a solid lipstick composition comprising at least one polypropyl silsesquioxane film forming resin, at least one silicone acrylate copolymer, at least one volatile hydrocarbon solvent, and at least one wax, wherein the ratio of the silicone acrylate copolymer to the polypropyl silsesquioxane resin is from about 1:1 to about 1:4, said composition preferably having a hardness of at least 40 gf for an 8.1 mm diameter stick.

18 Claims, No Drawings

SOLID LIPSTICK COMPOSITION HAVING IMPROVED HARDNESS

BACKGROUND OF THE INVENTION

The present invention relates to a solid lipstick composition comprising a polypropyl silsesquioxane film forming resin, a silicone acrylate copolymer, a volatile hydrocarbon solvent, a wax and colorant, wherein the ratio of the silicon acrylate copolymer to the polypropyl silsesquioxane resin is from about 1:1 to about 1:4, said composition preferably having a hardness of at least 40 gf for an 8.1 mm diameter stick.

The use of polyorganosiloxane-containing polymers in cosmetic compositions, including lipsticks, is discussed, for example in U.S. Pat. No. 7,879,316. The use of silicone acrylate copolymers and polypropylsilsesquioxane resins in liquid lipstick compositions has been described, for example, in US2007/0093619 and US2012/0301415.

It is desirable to use silicone polymers in combination with high amounts (e.g. greater than about 30%, more typically greater than 40%) of volatile hydrocarbon solvents in cosmetic compositions as these ingredients can improve the properties of such compositions. However, cosmetic compositions containing silicone polymers and high amounts of volatile hydrocarbon solvents are typically limited to liquid/gel formats due to the softening effects these polymers, as well as the volatile hydrocarbon solvents, have on the resulting compositions. Id. A high volatile solvent load makes it particularly challenging to achieve a solid lipstick with acceptable hardness.

There remains a need for a cosmetic composition, in particular a lipstick that includes a silicone polymer and a high amount of volatile hydrocarbon solvents and yet is hard enough to afford a solid format.

Surprisingly, applicants have found that combining a polypropylsilsesquioxane film forming resin with a silicone acrylate copolymer in a particular ratio counteracts the softening effect that the silicon polymer typically imparts to a cosmetic composition, thereby yielding a composition that is sufficiently hard so as to enable a solid format, such as a solid lipstick. It is also surprising that even with the high amount of volatile hydrocarbon solvents used to solubilize the silicone film former, the resulting composition still yields a solid lipstick, which when applied to lips and once the volatile solvents evaporate, yields a superior film with increased spread ability.

It is particularly surprising that the use of the polypropylsilsesquioxane film forming resin increases the hardness of the composition sufficiently to afford a solid lipstick even without the large amounts of waxes and fillers typically required as hardening agents. Most solid cosmetic compositions, particularly lipsticks, require either hardening ingredients (such as waxes and fillers) in amounts typically greater than about 15%, or the reduction of solvents, to afford solid compositions having acceptable hardness. In contrast, the compositions of the invention include high amounts of volatile solvents (greater than 30%, typically greater than 40%) and relatively low amounts of waxes and fillers (20% or less, typically less than 15%).

BRIEF SUMMARY OF THE INVENTION

The present invention relates to a cosmetic composition comprising:
(a) from about 1% to about 25% by weight of at least one silicone acrylate copolymer;
(b) from about 5% to about 35% by weight of at least one polypropylsilsesquioxane film forming resin;
(c) from about 10% to about 20% by weight of at least one wax;
(d) from about 30% to about 70% by weight of at least one volatile hydrocarbon solvent;
(e) optionally one colorant; and
(f) optionally at least one filler;
wherein the ratio of the silicon acrylate copolymer (a) to the at least one polypropylsilsesquioxane film forming resin (b) is from about 1:1 to about 1:4; the composition having a hardness of at least 40 gf; the weights being relative to the weight of the composition.

The invention also relates to a method for making up the lips by applying a composition comprising:
(a) from about 1% to about 25% by weight of at least one silicone acrylate copolymer;
(b) from about 5% to about 35% by weight of at least one polypropylsilsesquioxane film forming resin;
(c) from about 10% to about 20% by weight of at least one wax;
(d) from about 30% to about 70% by weight of at least one volatile hydrocarbon solvent;
(e) optionally one colorant; and
(f) optionally at least one filler;
wherein the ratio of the silicon acrylate copolymer (a) to the at least one polypropylsilsesquioxane film forming resin (b) is from about 1:1 to about 1:4; the composition having a hardness of at least 40 gf; the weights being relative to the weight of the composition.

DETAILED DESCRIPTION OF THE INVENTION

It has been unexpectedly discovered that a cosmetic composition containing at least one silicon acrylate copolymer and at least one polypropylsilsesquioxane film forming resin in a ratio of from about 1:1 to about 1:4 provides enhanced hardness of the composition.

Without being bound by theory, it is believed that the propyl substituted polymeric silsesquioxane film forming resin in combination with the silicone acrylate copolymer at the specific ratio range provides a stronger film.

The composition of the invention is particularly useful as a hard lipstick, which may be hot-poured and molded.

The lipstick compositions of the invention do not require, and preferably are free of thickeners, such as for example disteardimonium hectorite, and still provide excellent wear without color bleeding ("feathering") around the lips.

"About" as used herein means within 10% of the indicated number (e.g. "about 10%" means 9%-11% and "about 2%" means 1.8%-2.2%).

"At least one" means one or more and thus includes individual components as well as mixture/combinations.

"Comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

The term "film forming" means that the polypropylsilsesquioxane polymer is capable of forming a film, in particular, a substantive film, on the lips, for example after a solvent accompanying the film former has evaporated, absorbed into and/or dissipated on the lips.

"INCI" is an abbreviation of International Nomenclature of Cosmetic Ingredients, which is a system of names provided by the International Nomenclature Committee of the Personal Care Products Council to describe personal care ingredients.

By the term "resin" it is meant that the polypropylsilsesquioxane film forming polymer is an amorphous polymer having a low Tg of from about 0° C. to about 5° C. and has substantive film forming properties when applied to a keratinous material, such as the lips.

"Tackiness" as used herein refers to the adhesion between two substances. For example, the more tackiness there is between two substances, the more adhesion there is between the substances. To quantify "tackiness" it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

The "wear" of compositions as used herein, refers to the extent by which the color of the composition remains the same or substantially the same as at the time of application, as viewed by the naked eye, after a certain period or an extended period of time. Wear properties may be evaluated by any method known in the art for evaluating such properties. For example, wear may be evaluated by a test involving the application of a composition to human lips and evaluating the color of the composition after a specified period of time. For example, the color of a composition may be evaluated immediately following application to skin or lips and these characteristics may then be re-evaluated and compared after a certain amount of time. Further, these characteristics may be evaluated with respect to other compositions, such as commercially available compositions.

All percentages, parts and ratios herein are based upon the total weight of the compositions of the present invention, unless otherwise indicated.

As used herein, all ranges provided are meant to include every specific range within, and combination of subranges between, the given ranges. Thus, a range from 1-5, includes specifically 1, 2, 3, 4 and 5, as well as subranges such as 2-5, 3-5, 2-3, 2-4, 1-4, etc.

As used herein a range of ratios is meant to include every specific ratio within, and combination of subranges between, the given ranges.

According to various embodiments of the disclosure, the weight percent ratio of the at least one silicon acrylate copolymer (a) to the at least one polypropylsilsesquioxane film forming resin (b) is from about 1:1 to about 1:4, such as from about 1:1 to about 1:3, and from about 1:1 to about 1:2, and from about 1:2 to about 1:4, and about 1:3 to about 1:4.

In various embodiments, the weight percent ratio of (a) to (b) is 1:1, or 1:2 or 1:3 or 1:4.

In particular embodiments, the weight percent ratio of (a) to (b) is about 1:1 or about 1:2.2, in particular about 1:2.2.

The hardness the compositions herein is expressed in gramforce (gf). The inventive compositions of the present invention have a hardness of at least 40 gf, typically from about 40 gf to about 300 gf, most typically from about 40 gf to about 175 gf.

The hardness of the compositions was assessed using the "cheese wire" method. This method involves cutting an 8.1 mm diameter stick composition (also known as a "slim bullet") or a 12.7 mm in diameter stick composition (also known as a "chubby bullet") and measuring its hardness at 20° C. using a tensile testing machine (dynamometer) from Chatillon Ametek at a speed of 100 mm/minute. The hardness value from this method is expressed in grams as the shear force required to cut a stick under the above conditions. According to this method, the hardness of compositions according to the present invention which may be in stick form may, for example, range from about 40 gf to about 250 gf, more typically from about 40 gf to about 100 gf, most typically from about 40 gf to about 70 gf, for a sample of 8.1 mm diameter stick, and further such as from about 75 gf to about 300 gf, more typically from about 75 gf to 175 gf for a sample of 12.7 mm diameter stick.

Unless otherwise indicated, hardness values provided herein are for an 8.1 mm diameter stick ("slim" stick).

The hardness of the composition of the present invention preferably is such that the compositions are self-supporting and can easily disintegrate to form a satisfactory deposit on the lips. In addition, this hardness imparts good impact strength to the inventive compositions, which may be molded or cast, for example, in stick or dish form.

The cosmetic compositions and methods of the present invention can comprise, consist of, or consist essentially of the essential elements and limitations of the invention described herein, as well as any additional or optional ingredients, components, or limitations described herein or otherwise useful in personal care.

In an embodiment the present invention relates to a cosmetic composition comprising:
(a) from about 1% to about 25% by weight of at least one silicone acrylate copolymer;
(b) from about 5% to about 35% by weight of at least one polypropylsilsesquioxane film forming resin;
(c) from 10% to about 20% by weight of at least one wax;
(d) from about 30% to about 70% by weight of at least one volatile hydrocarbon solvent;
(e) optionally least one colorant; and
(f) optionally at least one filler;
wherein the ratio of the silicon acrylate copolymer (a) to the at least one polypropylsilsesquioxane film forming resin (b) is from about 1:1 to about 1:4; the composition having a hardness of at least 40 gf; the weights being relative to the weight of the composition.

In another embodiment the invention relates to a composition comprising
(a) from about 1% to about 25% by weight of at least one silicone acrylate copolymer;
(b) from about 5% to about 35% by weight of at least one polypropylsilsesquioxane film forming resin;
(c) from 10% to about 20% by weight of at least one wax;

(d) from about 30% to about 70% by weight of at least one volatile hydrocarbon solvent;
(e) from about 0.5% to about 15% by weight of least one colorant; and
(f) optionally at least one filler;
wherein the ratio of the silicon acrylate copolymer (a) to the at least one polypropylsilsesquioxane film forming resin (b) is from about 1:1 to about 1:4; the composition having a hardness of at least about 40 gf; the weights being relative to the weight of the composition.

In another embodiment the sum of the weight percent of the at least one silicone acrylate copolymer (a) plus the at least one polypropylsilsesquioxane film forming resin (b) is less than or equal to 20% [(a)+(b) 20%]. Having a total amount of film forming resins at less than 20% improves comfort as it yield a lipstick that has a less tacky (and thus more desirable) feel when applied to the lips.

In another embodiment the compositions according to the invention contain greater that about 40%, more particularly greater than 50%, volatile hydrocarbon solvents.

In another embodiment the invention relates to a composition comprising
(a) from about 1% to about 25% by weight of at least one silicone acrylate copolymer;
(b) from about 5% to about 35% by weight of at least one polypropylsilsesquioxane film forming resin;
(c) from 10% to about 20% by weight of at least one wax;
(d) from about 50% to about 60% by weight of at least one volatile hydrocarbon solvent;
(e) from about 0.5% to about 15% by weight of at least one colorant; and (f) optionally at least one filler;
wherein the ratio of the silicon acrylate copolymer (a) to the at least one polypropylsilsesquioxane film forming resin (b) is from about 1:1 to about 1:3; the sum of (a)+(b) is less than or equal to 20%; the composition having a hardness of at least about 40 gf; the weights being relative to the total weight of the composition.

The Silicone Acrylate Copolymer (a)

The compositions of the present invention comprise at least one silicone acrylate copolymer.

The at least one silicone acrylate copolymer polymer can be chosen from silicone/(meth)acrylate copolymers, such as those as described in U.S. Pat. Nos. 5,061,481, 5,219,560, 5,262,087 and US 2012/0301415, the entire contents of which are hereby incorporated by reference. They may also be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (tentative INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples include polymers comprising a backbone chosen from vinyl polymers, methacrylic polymers, and acrylic polymers and at least one chain chosen from pendant siloxane groups and pendant fluorochemical groups. Non-limiting examples of such polymers and their synthesis are disclosed, for example, in U.S. Pat. Nos. 4,972,037, 5,061,481, 5,209,924, 5,849,275, and 6,033,650, and WO 93/23446, WO 95/06078 and WO 01/32737, the disclosures of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate polymers include silicone/acrylate graft terpolymers, for example, the copolymers described in WO 01/32727 A1, the disclosure of which is hereby incorporated by reference.

According to other embodiments, the polymer comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, and 4,981,902, the disclosures of which are hereby incorporated by reference.

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

In an embodiment the silicone acrylate copolymer has a glass transition temperature (Tg) above 20° C.

In another embodiment, the silicone acrylate copolymer is an acrylates/dimethicone copolymer having a Tg above 20° C.

The silicone acrylate polymers (a) may be present in the composition of the invention in an amount ranging from about 1% to about 25% by weight, preferably from 2 to 15% by weight, more preferably from about 3% to about 9% by weight, and more preferably from about 4% to about 8.5% by weight, including all ranges and subranges therebetween, based on the weight of the total composition.

The Polypropylsilsesquioxane Film Forming Resin (b)

The compositions of the present invention comprise at least one polypropyl silsesquioxane film forming resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film forming resin is made up predominantly of tri-functional units (or T units), it is generally called a silsesquioxane resin. See, US2006/0292096.

Examples of silsesquioxane resins that may be used in the present invention are alkyl silsesquioxane resins that are silsesquioxane homopolymers and/or copolymers having an average siloxane unit of the general formula $R^1 \text{ n SiO}(4-n)/2$, wherein each $R^1$ is a propyl group, wherein more than 80 mole % of R1 represent a C3-C10 alkyl group, n is a value of from 1.0 to 1.4, and more than 60 mole % of the copolymer comprises $R1SiO3/2$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference in their entirety.

A non-limiting example of a polypropylsilsesquioxane resin suitable for use in the present invention is commercially available from Dow Corning as Dow Corning 670 and Down Corning 680 Fluid. Dow Corning 670 and 680 Fluids have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight.

The film forming polypropylsilsesquioxane resin (b) may be present in the instant compositions in an amount ranging from about 5% to about 35% by weight, preferably from about 7% to about 30% by weight, more preferably from about 7.4% to about 11% by weight, including all ranges and subranges therebetween, based on the weight of the total composition.

Wax (c)

The compositions of the present invention comprise at least one wax.

For the purposes of the present invention, a wax is a lipophilic fatty compound that is solid at room temperature (25° C.), has a reversible solid/liquid change of state (that is, the state of the material may change based on temperature), has a melting point greater than 45° C., preferably greater than 55° C., more preferably between about 65° C. to about 120° C., and has anisotropic crystal organization in the solid state. For the purposes of this invention, the waxes are those generally used in cosmetics and dermatology. The waxes may be of natural origin, for instance beeswax, carnauba wax, candelilla wax, ouricoury wax, Japan wax, cork fiber wax or sugar cane wax, paraffin wax, lignite wax, microcrystalline waxes, lanolin wax, montan wax, ozokerites and hydrogenated oils, for instance hydrogenated jojoba oil.

The waxes may also be of synthetic origin, for instance polyethylene waxes derived from the polymerization of ethylene, waxes obtained by Fischer-Tropsch synthesis, esters of fatty acids and of glycerides. These waxes are solid at 40° C.

Waxes of synthetic origin are preferable as they are more uniform and provide greater reproducibility than waxes of natural origin. Moreover, the waxes are preferably not silicone waxes.

The at least one wax may be present in the instant compositions in an amount ranging from about 10% to about 20% by weight, preferably from about 11.5% to 15% by weight, including all ranges and subranges therebetween, all weights based on the weight of the composition as a whole.

The Volatile Hydrocarbon Solvent (d)

The cosmetic compositions of the present invention also contain at least one volatile hydrocarbon solvent.

As used herein "volatile hydrocarbon solvent" means a non-aqueous organic medium capable of evaporating on contact with the skin or the lips in less than one hour at room temperature and atmospheric pressure. "Volatile" solvents typically have a flash point of less than about 100° C.

Non-limiting examples of suitable volatile hydrocarbon solvents include volatile hydrocarbon-based oils having from 8 to 16 carbon atoms, and mixtures thereof, and in particular branched $C_8$ to $C_{16}$ alkanes such as $C_8$ to $C_{16}$ isoalkanes (also known as isoparaffins), such as isododecane, isodecane, isohexadecane, which are commercially available under the trade names of Isopar or Permethyl. Also useful are $C_8$ to $C_{16}$ branched esters, such as isohexyl or isodecyl neopentanoate, as well as alcohols, and mixtures of these compounds. Preferably, the volatile hydrocarbon-based oils have a flash point of at least 40° C.

Examples of suitable volatile hydrocarbon-based oils include, but are not limited to, those given in Table 1 below.

TABLE 1

| Compound | Flash Point (° C.) |
| --- | --- |
| Isododecane | 43 |
| Isohexadecane | 102 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

In a preferred embodiment, the volatile hydrocarbon solvent is selected from isododecane, isooctane, dodecane, isohexadecane, and mixtures thereof.

The at least one volatile hydrocarbon solvent is generally present in the cosmetic composition of the present invention in an amount ranging from about 30% to about 70% by weight; such as from about 40% to about 65% by weight; such as from about 45% to about 60% by weight; including all ranges and subranges therebetween, all weights being based on the weight of the composition as a whole.

Non-Volatile Solvent (Optional)

The cosmetic compositions of the present invention optionally may also contain one or more non-volatile solvents.

Suitable non-volatile solvents include, but are not limited to, various types of oils. Mention may be made of hydrocarbon-based oils such as liquid paraffin or liquid petroleum jelly, mink oil, turtle oil, soybean oil, perhydrosqualene, sweet almond oil, beauty-leaf oil, palm oil, grape seed oil, sesame seed oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl alcohol or linolenyl alcohol, isostearyl alcohol or octyldodecanol; silicone oils such as polydimethylsiloxanes (PDMS), which are optionally phenylated such as phenyltrimethicones, trimethyl pentaphenyl siloxane, tetramethyl tetraphenyl siloxane, or optionally substituted with aliphatic and/or aromatic groups that are optionally fluorinated, or with functional groups such as hydroxyl, thiol and/or amine groups; polysiloxanes modified with fatty acids, with fatty alcohols, with polyoxyalkylenes or with hydrocarbyl functional groups, fluorosilicones and perfluoro oils.

The non-volatile solvent may be present in the compositions of the invention from about 1% to about 40% by weight, most typically from about 5% to about 10% by weight, including all ranges and subranges therebetween, relative to the weight of the composition.

The Colorant (e)(Optional)

The cosmetic compositions of the present invention optionally may contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation. However, one preferred amount of colorant for use in the present invention is from about 0.5% to about 15.7% by weight, including all ranges and subranges therebetween, relative to the weight of the composition.

The Filler(s) (f) (Optional)

The cosmetic compositions of the present invention optionally may contain at least one cosmetically acceptable filler. Examples of useful fillers include mica; silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride sold under the name Dry-Flo by the company National Starch; silicone resin microbeads such as those sold under the name Tospearl by the company Toshiba Silicone; clays (bentone, laponite, saponite, etc.); and mixtures thereof.

The fillers may be present in the composition of the invention in an amount ranging from about 0.1% to about 10% by weight, such as from 0.5% to about 8% by weight, and such as from about 1% to about 5% by weight, including all ranges and subranges therebetween, all weights based on the weight of the composition as a whole.

Additional Optional Additives/Auxiliary Agents

The compositions of the present invention may further comprise any cosmetically or dermatologically acceptable additional additives such as thickeners/viscosity increasing agents, additional film formers, plasticizers, antioxidants, essential oils, preserving agents, fragrances, additonal fillers, pasty fatty substances, additional waxes, neutralizing agents, emollients, moisturizers, vitamins, essential fatty acids, sunscreens, surfactants, medicaments, and mixtures thereof. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

If present, these additives may be present in the composition in a proportion from 0% to 99% by weight, such as from 0.01% to 90% by weight, and further such as from 0.1% to 50% by weight, including all ranges and subranges therebetween, relative to the total weight of the composition.

It has been surprisingly discovered that the association of a silicone acrylate copolymer and a polypropylsilsesquioxane film forming resin in a ratio of from about 1:1 to about 1:4, in the presence of a high amount of volatile hydrocarbon solvents (30% or higher, typically 40% or higher) and low amount of waxes and/or fillers (less than 20%, typically less than 15%) yields a solid lipstick having improved hardness.

The compositions of the present invention are useful as compositions for making up the skin, in particular the lips.

The present invention will be better understood from the examples which follow, all of which are intended for illustrative purposes only.

EXAMPLES

Lipstick compositions in accordance with the present invention as well as comparator and control compositions were prepared as described below. The ingredients employed in each example are provided in Table 2.

TABLE 2

Sample Lipsticks (Solid)

| Compound | Example 1 (Comparator) (Amt %) | Example 2 (Amt %) | Example 3 (Amt %) | Control 1 | Control 2 |
|---|---|---|---|---|---|
| acrylates/dimethicone copolymer (40% active) (a) (60% solvent-isododecane) (KP550, Shin Etsu) | 11.2 (a) 16.8 | 8 (a) 12 | 4.8(a) 7.2 | 0 | 16 (a) 24 |
| poly propylsilsesquioxane (72%) (b) (and) isododecane (28%) (Dow Corning 680 ID Fluid) | 4.61 (b) 1.79 | 7.68 (b) 2.99 | 10.75 (b) 4.18 | 15.36 (b) 5.97 | 0 |
| polyethylene wax (c) (Performalene 500-L Polyethylene, New Phase Technologies) | 12 | 12 | 12 | 12 | 12 |
| isododecane (d) QS | 43.6 | 47.33 | 51.07 | 56.67 | 38 |
| red 7 (e) | 5 | 5 | 5 | 5 | 5 |
| mica | 5 | 5 | 5 | 5 | 5 |
| (a):(b) | 2.43:1 | 1.04:1 | 1:2.24 | — | — |

Preparation of Lipsticks

Polymer solutions, resin, waxes, and a portion of isododecane were blended under high shear at 110° C. until all materials were completely blended. The solution temperature was brought down to 65° C. and pigment solution, mica and the final amount of isododecane was added to the mixture and blended until homogenous. Mixtures were poured in a slim lipstick mold and allowed to reach room temperature over the course of 30 minutes. The mold was then chilled on a cooling plate for an addition 20 minutes. Sticks were individually transferred into standard lipstick compartments and allowed to equilibrate at room temperature for 24 hours.

Hardness Testing

After equilibrating at room temperature for 24 hours, sample hardness was assessed using the "cheese wire" method as described above. Table 3 below provides the average hardness collected for 8 lipsticks per respective sample type.

TABLE 3

Hardness values for lipsticks

| Measurement | Ex. 1 | Ex. 2 | Ex. 3 | Control 1 | Control 2 |
|---|---|---|---|---|---|
| Hardness (gf) | NS* | 52.92 | 41.7 | 22.87 | |
| Standard Deviation | NS* | 3.54 | 3.02 | 0.987 | |

*In Table 3, "NS" means no stick was formed

As is shown in Table 3, samples containing polypropylsilsesquioxane ("T-Propyl") resin and no acrylates/dimethicone copolymer (e.g. KP 550) (Control 1) resulted in a soft stick with an average hardness of 22.87 gf. Sticks containing acrylates/dimethicone (KP550) and no polypropylsilsesquioxane resin (e.g. T-Propyl) (Control 2) were too soft to form a stick.

It was unexpectedly found that within a ratio (a):(b) of from about 1:1 to about 1:4, a stick was formed that had an increased hardness relative to lipsticks containing just a single component (a) or (b) (Controls 1 and 2), or had both components but the ratio was outside the claimed ratio (Example 1, where no stick was formed).

What is claimed is:

1. A solid lipstick composition comprising:
   (a) from about 1% to about 25% by weight of at least one acrylates/dimethicone copolymer;
   (b) from about 5% to about 35% by weight of at least one polypropylsilsesquioxane film forming resin;
   (c) from 10% to about 20% by weight of at least one synthetic wax;
   (d) at least one volatile hydrocarbon solvent selected from the group consisting of isododecane, isooctane, dodecane, isohexadecane, and mixtures thereof, and
   (e) at least one phenylated silicone oil;
   wherein the polypropylsilsesquioxane film forming resin has the general formula $RnSiO(4-n)/2$; wherein R is independently chosen from a hydrogen atom and a monovalent hydrocarbon group comprising 3 carbon atoms, wherein more than 80 mole % of R are propyl groups; n is a value from 1.0 to 1.4; more than 60 mole % of the resin comprises $RSiO3/2$ units; said film forming resin having a hydroxyl or alkoxy content from 0.2 to 10% by weight of the resin, and mixtures thereof; and wherein the ratio of the acrylates/dimethicone copolymer (a) to the at least one polypropylsilsesquioxane film forming resin (b) is from about 1:1 to about 1:4; the composition having a hardness of at least 40 gf; the weights being relative to the weight of the composition.

2. The composition of claim 1 wherein the sum of the weight percent of the at least one acrylates/dimethicone copolymer (a) and the at least one polypropylsilsesquioxane film forming resin (b) is less than or equal to 20%.

3. The composition of claim 2 wherein the acrylates/dimethicone copolymer is present in a product selected from the group consisting of cyclopentasiloxane (and) acrylates/dimethicone copolymer, butyl acetate (and) acrylates/dimethicone copolymer, methyl trimethicone (and) acrylates/dimethicone copolymer) and isododecane (and) acrylate/dimethicone copolymer, and mixtures thereof.

4. The composition of claim 3 wherein the polypropylsilsesquioxane film forming resin has the general formula $RnSiO(4-n)/2$; wherein R is independently chosen from a hydrogen atom and a monovalent hydrocarbon group comprising 3 carbon atoms, wherein more than 80 mole % of R are propyl groups; n is a value from 1.0 to 1.4; more than 60 mole % of the resin comprises $RSiO3/2$ units; said film forming resin having a hydroxyl or alkoxy content from 0.2 to 10% by weight of the resin, and mixtures thereof.

5. The composition of claim 1 wherein the wax is selected from the group consisting of polyethylene wax, stearoxydimethicone, behenoxy dimethicone, stearyl dimethicone, cetearyl dimethicone, and mixtures thereof.

6. The composition of claim 5 comprising greater than 40% volatile hydrocarbon solvents.

7. The composition of claim 6 wherein a volatile hydrocarbon solvent is isododecane.

8. The composition of claim 7 further comprising at least one colorant.

9. The composition of claim 8 wherein the ratio of the acrylates/dimethicone copolymer (a) to the at least one polypropylsilsesquioxane film forming resin (b) is from about 1:1 to about 1:2.5.

10. The composition of claim 9 having a hardness of from about 40 gf to about 100 gf.

11. A solid lipstick composition comprising:
(a) from about 1% to about 25% by weight of acrylate/dimethicone copolymer;
(b) from about 5% to about 35% by weight of polypropylsilsesquioxane film forming resin;
(c) from 10% to about 20% by weight of synthetic polyethylene wax;
(d) isododecane;
(e) at least one colorant, and
(f) at least one phenylated silicone oil;
wherein the polypropylsilsesquioxane film forming resin has the general formula RnSiO(4−n)/2; wherein R is independently chosen from a hydrogen atom and a monovalent hydrocarbon group comprising 3 carbon atoms, wherein more than 80 mole % of R are propyl groups; n is a value from 1.0 to 1.4; more than 60 mole % of the resin comprises RSiO3/2 units; said film forming resin having a hydroxyl or alkoxy content from 0.2 to 10% by weight of the resin, and mixtures thereof; and wherein the ratio of the acrylate/dimethicone copolymer (a) to the polypropylsilsesquioxane film forming resin (b) is from about 1:1 to about 1:2.5; the sum of the weight percent of the at least one silicone acrylate copolymer (a) and the at least one polypropylsilsesquioxane film forming resin (b) is less than or equal to 20%; the composition having a hardness of from about 40 gf to about 70 gf; the weights being relative to the weight of the composition.

12. A method of making up lips comprising applying to the lips a solid lipstick composition in an amount effective to make up the lips comprising:
(a) from about 1% to about 25% by weight of at least one acrylates/dimethicone copolymer;
(b) from about 5% to about 35% by weight of at least one polypropylsilsesquioxane film forming resin;
(c) from 10% to about 20% by weight of at least one synthetic wax;
(d) at least one volatile hydrocarbon solvent selected from the group consisting of isododecane, isooctane, dodecane, isohexadecane, and mixtures thereof;
(e) at least one colorant, and (f) at least one phenylated silicone oil;
wherein the polypropylsilsesquioxane film forming resin has the general formula RnSiO(4−n)/2; wherein R is independently chosen from a hydrogen atom and a monovalent hydrocarbon group comprising 3 carbon atoms, wherein more than 80 mole % of R are propyl groups; n is a value from 1.0 to 1.4; more than 60 mole % of the resin comprises RSiO3/2 units; said film forming resin having a hydroxyl or alkoxy content from 0.2 to 10% by weight of the resin, and mixtures thereof; and wherein the ratio of the acrylates/dimethicone copolymer (a) to the at least one polypropylsilsesquioxane film forming resin (b) is from about 1:1 to about 1:4; the composition having a hardness of at least 40 gf; the weights being relative to the weight of the composition.

13. The composition of claim 1 wherein the composition is free of silicone wax.

14. The composition of claim 11 wherein the composition is free of silicone wax.

15. The method of claim 12 wherein the composition is free of silicone wax.

16. The method of claim 12 wherein the composition has a hardness of from about 40 gf to about 100 gf.

17. The composition of claim 10 wherein the composition is free of silicone wax.

18. The method of claim 16 wherein the composition is free of silicone wax.

* * * * *